(12) United States Patent
Nakauchi et al.

(10) Patent No.: US 8,546,141 B2
(45) Date of Patent: Oct. 1, 2013

(54) METHOD FOR PREPARATION OF PLATELET FROM IPS CELL

(75) Inventors: Hiromitsu Nakauchi, Tokyo (JP); Koji Eto, Tokyo (JP); Hidekazu Nishiki-I, Tokyo (JP); Naoya Takayama, Tokyo (JP); Shinya Yamanaka, Kyoto (JP); Kazutoshi Takahashi, Kyoto (JP)

(73) Assignee: The University of Tokyo, Tokyo (JP)

(*) Notice: Subject to any disclaimer, the term of this patent is extended or adjusted under 35 U.S.C. 154(b) by 0 days.

(21) Appl. No.: 12/935,380

(22) PCT Filed: Apr. 1, 2009

(86) PCT No.: PCT/JP2009/001542
§ 371 (c)(1), (2), (4) Date: Nov. 9, 2010

(87) PCT Pub. No.: WO2009/122747
PCT Pub. Date: Oct. 8, 2009

(65) Prior Publication Data
US 2011/0053267 A1    Mar. 3, 2011

(30) Foreign Application Priority Data
Apr. 1, 2008    (JP) ................. 2008-094584

(51) Int. Cl.
*C12N 5/00*    (2006.01)
*C12N 15/00*    (2006.01)

(52) U.S. Cl.
USPC ............ 435/377; 435/372; 435/373; 435/455

(58) Field of Classification Search
USPC ........................................ 435/377, 372, 373
See application file for complete search history.

(56) References Cited

U.S. PATENT DOCUMENTS

| 2006/0099198 A1 | 5/2006 | Thomson et al. |
| 2007/0077654 A1 | 4/2007 | Thomson et al. |

FOREIGN PATENT DOCUMENTS

| JP | 2004350601 | 12/2004 |
| JP | 2005511084 | 4/2005 |
| JP | 2005287478 | 10/2005 |
| JP | 2005287479 | 10/2005 |
| JP | 2006061106 | 3/2006 |
| JP | 2006141356 | 6/2006 |
| JP | 2007089432 | 4/2007 |
| WO | 03050251 | 6/2003 |
| WO | 2005019441 | 3/2005 |
| WO | 2007069666 | 6/2007 |
| WO | 2008041370 | 4/2008 |
| WO | 2009119105 | 10/2009 |

OTHER PUBLICATIONS

Gekas and Graf JEM, 2010, 2781-2784.*
Gaur, J Thromb Haemost 2006; 4: 436-42.*
Hirashima et al, Blood, 1999, 1253-1263.*
Kaushansky, J. Clin. Invest. 115:3339-3347.*
Takayama et al Blood 2008 111: 5298-5306, online Apr. 3, 2008.*
Takayama, et al Blood ASH Annual Meeting Abstracts) (2006), vol. 108, No. 11, p. 474a, Abstract 1665, Poster Board#session: 793-1.*
Yu et al Science, 2007, 1917-1920.*
Okamoto et al J Artif Organs (2004) 7:194-202.*
Choi et al (J Expt. Medicine, Mar. 5, 2009, 559-567).*
Takahashi et al (Cell . Nov. 30, 2007;131(5):861-72.*
Schenke-Layland et al (Stem cell, 2008, 26, 1537-1546.*
Hanna et al (Science, 2007, 318, 1920-1923.*
Eto et al., Proc. Acad. Sci. USA 2002, 99: 12819-12824.
Fujimoto et al., Blood 200, 102: 4044-4051.
Hiroyama et al., Exp. Hematol. 2006, 34: 760-769.
Gaur et al., J Thromb. Haemost. 2005, 4: 436-442.
Okita et al., Nature 2007, 448: 313-317.
Wernig et al., Nature 2007, 448: 318-324.
Maherali et al., Cell Stem Cell 2007, 1: 55-70.
Nakagawa et al., Nat. Biotechnol. 2008, 26: 101-106.
Yu et al., Science 2007, 318: 1917-1920.
Takahashi et al., Cell 2007, 131: 861-872.
Takayama et al., BLOOD 2008, 111: 5298-5306.
Bergmeier, W. et al., Cir Res 95: 677-683, 2004.
Gardiner, EE et al., J Thrombosis and Haemostasis, 5: 1530-1537, 2007.
Jiang J., et al., High dose chemotherapy and transplantation of hematopoietic progenitors from murine D3 embryonic stem cells., Journal of Chemotherapy (2005), vol. 17, No. 3, pp. 302-308.
Yuka Nagata, Thrombopoietin ni yoru Tabaitaika o Tomonau Kyokakukyu Tokuiteki na Bunka Seijuku Katei no Kaiseki, Research Reports of Uehara Memorial Foundation (1999), vol. 13, pp. 89-91. (With English Translation.).
Takayama, et al., Human Embryonic Stem Cell-Derived "NET-Like" Structure Serves as a Hematopoietic Progenitor Niche and Favors Generation of Mature Megakaryocytes and Functional Platelets, Blood (ASH Annual Meeting Abstracts) (2006), vol. 108, No. 11, p. 474a, Abstract 1665, Poster Board#session: 793-I.
Takayama, et al., Hito ES Saibo Yurai Zoketsu Shiji Kozotai: Nojo Kozobutsu (ES-Sac) Karano Ketsueki Saibo no Bunka Yudo, Rinsho Ketsueki (2007), vol. 48, No. 9, p. 936.
Cheng et al., "Human Mesenchymal Stem Cells Support Megakaryocyte and Pro-Platelet Formation From CD34+ Hematopoietic Progenitor Cells",Journal of Cellular Physiology, 184:58-69 (2000).
Huyhn et al., "Characterization of hematopoietic progenitors from human yolk sacs and embryos", Blood Journal, 1995 86: 4474-4485.
Hirashima et al., "Maturation of Embryonic Stem Cells Into Endothelial Cells in an In Vitro Model of Vasculogenesis", Blood Journal, 1999 93:1253-1263.
Vodyanik et al., "Human embryonic stem cell-derived CD34+ cells: efficient production in the coculture with OP9 stromal cells and analysis of lymphohematopoietic potential", 2005, 105: 617-626.

(Continued)

Primary Examiner — Anoop Singh
(74) Attorney, Agent, or Firm — Pearne & Gordon LLP

(57) ABSTRACT

A method for efficiently preparing blood cells, such as mature megakaryocytes and platelets, from iPS cells is achieved in an in vitro culture system. A sac-like structure encloses hematopoietic progenitor cells, which is obtained by inoculating iPS cells onto feeder cells and then culturing the iPS cells under conditions suitable for inducing the differentiation of hematopoietic progenitor cells. Moreover, a method for producing various types of blood cells, comprises culturing hematopoietic progenitor cells enclosed in the sac-like structure under conditions suitable for inducing the differentiation of blood cells. Furthermore, a method for producing various types of blood cells, particularly megakaryocytes and platelets, is achieved without involving the sac-like structure.

3 Claims, 9 Drawing Sheets

(56) References Cited

OTHER PUBLICATIONS

Chinese Examination Report corresponding to Application No. 200780038694.6, dated Jul. 5, 2010.
GB Examination Report corresponding to Application No. GB0906137.5, dated Aug. 4, 2010.
Non-Final Office Action dated Sep. 17, 2010 from corresponding/related U.S. Appl. No. 12/444,237, filed Jun. 10, 2009.
Final Office Action dated Feb. 17, 2011 from corresponding/related U.S. Appl. No. 12/444,237, filed Jun. 10, 2009.
Fujimoto et al., "Production of functional platelets by differentiated embryonic stem (ES) cells in vitro", Blood 2003, 102: 4044-4051.
Chinese Examination Report dated Sep. 26, 2011 for 200980111520.7 with English translation.
Hanna, et al., "Treatment of Sickle Cell Anemia Mouse Model with iPS Cells Generated from Autologous Skin"; Science, Dec. 21, 2007, vol. 318; pp. 1920-1923.
Scheneke-Layland et al., "Reprogrammed Mouse Fibroblasts Differentiate into Cells of the Cardiovascular and Hematopoietic Lineages"; Stem Cells 2008; 26:1537-1546.
Nishikii, et al."Metalloproteinase regulation improves in vitro generation of efficacious platelets from mouse embryonic stem cells"; The Journal of Experimental Medicine 2008: vol. 205, No. 8; 1917-1927.
Saeki, et al., "Highly Efficient and Feeder-Free Production of Subculturable Vascular Endothelial Cells From Primate Embryonic Stem Cells"; Journal of Cellular Physiology: 2008: pp. 261-280.
The Supplemental European Search Report issued in European Application No. EP 09 72 7938.

* cited by examiner n : Neutrophil
m : Macrophage
E : Erythroblast
mix : Mixture Human PB-derived platelet Human ESCs-derived platelets Human iPSCs-derived platelets Platelets releasing from megakaryocyte

METHOD FOR PREPARATION OF PLATELET FROM IPS CELL

TECHNICAL FIELD

The present invention relates to a method for preparing platelets from iPS cells (induced pluripotent stem cells).

BACKGROUND ART

For the treatment of blood-related diseases including leukemia as a typical example, it is extremely important to stably amplify and supply blood cells in an amount necessary for such treatment. Thus, to date, many researchers have attempted to efficiently amplify hematopoietic stem cells or hematopoietic progenitor cells. Among blood cells, megakaryocytes are cells capable of producing proplatelets, and further, platelets. Hence, the megakaryocytes play an important role in medical treatments.

Among blood cells, platelets are cells essential for blood coagulation (hemostasis). Accordingly, the demand for platelets is extremely high in the treatment of leukemia, bone marrow transplantation, anticancer therapy, etc. To date, the platelets have been supplied by a method of collecting blood from blood donors. However, it is difficult for the method of collecting blood from blood donors to stably supply platelets, since this method is problematic in terms of chronic shortage of donors, inability to preserve the collected platelets in a frozen state, etc. At the same time, other than the method of collecting blood from blood donors, a method of administering TPO to patients, a method of differentiating megakaryocytes from umbilical cord blood or myelocytes, etc. have been attempted. However, in the case of the method of administering TPO to patients, antibodies neutralizing the TPO are produced after the administration of the TPO. Thus, this method has not yet been put to practical use. Also, the method of differentiating megakaryocytes from umbilical cord blood or myelocytes is not suitable as a method of stably providing platelets because it is able to provide only small quantities of hematopoietic stem cells serving as a source of megakaryocytes.

In recent years, as a method for preparing platelets in vitro, there has been reported, for example, a method for efficiently differentiating hematopoietic stem cells or hematopoietic progenitor cells, which are induced from ES cells, into megakaryocytes and platelets. Eto et al. have clarified that mouse ES cells are co-cultured with OP9 stromal cells, so as to induce the differentiation of the mouse ES cells into megakaryocytes (Non-Patent Document 1). Fujimoto et al. have reported that they have confirmed the induction of platelets by applying a method similar to that of Eto et al. (Non-Patent Document 2). Moreover, there has been a report regarding a successful induction of the differentiation of monkey ES cells into megakaryocytes (Non-Patent Document 3), and there has also been a report regarding a successful induction of the differentiation of human ES cells into megakaryocytes (Non-Patent Document 4). However, in both cases, the release of platelets has not been confirmed. Furthermore, even in a case in which a method of obtaining platelets from ES cells has been established to such an extent that it can be clinically applied, when the platelets induced from ES cells are applied to patients via blood transfusion (wherein the application of the platelets may not become problematic after the initial transfusion, but if a single patient frequently receives transfusions,) problems regarding human leukocyte antigen (HLA) compatibility still remain.

iPS cells (induced pluripotent stem cells) may also be referred to as artificial pluripotent stem cells or induced type pluripotent stem cells. These are cells that have acquired pluripotent differentiation ability equivalent to that of ES cells by introducing several types of transcription factor genes into somatic cells such as fibroblasts.

Mouse iPS cells have been established for the first time by Yamanaka et al. by introducing four genes, Oct3/4, Sox2, Klf4 and c-Myc, into mouse fibroblasts, using the expression of a Nanog gene important for the maintenance of pluripotency as an indicator (Non-Patent Document 5). After that, several reports have been made concerning the establishment of mouse iPS cells by similar methods (Non-Patent Documents 6 and 7). Further, it has been reported that iPS cells can be established only using the three genes (Oct3/4, Sox2 and Klf4) other than the c-Myc gene, in order to overcome problems regarding the canceration of iPS cells (Non-Patent Document 8).

On the other hand, with regard to human iPS cells, Thomson et al. have introduced OCT3/4, SOX2, NANOG and LIN28 into human fibroblasts, so as to establish human iPS cells (Non-Patent Document 9). In addition, Yamanaka et al. have introduced OCT3/4, SOX2, KLF4 and cMYC into human fibroblasts, so as to establish iPS cells (Non-Patent Document 10).

Non-Patent Document 1: Eto et al., Proc. Acad. Sci. USA 2002, 99: 12819-12824.

Non-Patent Document 2: Fujimoto et al., Blood 2003, 102: 4044-4051.

Non-Patent Document 3: Hiroyama et al., Exp. Hematol. 2006, 34: 760-769.

Non-Patent Document 4: Gaur et al., J Thromb Haemost. 2005, 4: 436-442.

Non-Patent Document 5: Okita et al., Nature 2007, 448: 313-317.

Non-Patent Document 6: Wernig et al., Nature 2007, 448: 318-324.

Non-Patent Document 7: Maherali et al., Cell Stem Cell 2007, 1: 55-70

Non-Patent Document 8: Nakagawa et al., Nat. Biotechnol. 2008, 26: 101-106.

Non-Patent Document 9: Yu et al., Science 2007, 318: 1917-1920.

Non-Patent Document 10: Takahashi et al., Cell 2007, 131: 861-872.

DISCLOSURE OF THE INVENTION

Problems to be Solved by the Invention

The present inventors had already established a method for efficiently obtaining megakaryocytes and platelets from ES cells. In the case of using ES cells, the efficiency of inducing megakaryocytes and platelets differs depending on the ES cells used. If ES cells having a high efficiency of inducing megakaryocytes and platelets can be selected at an early stage, it becomes possible to achieve stabilization of the efficiency of obtaining megakaryocytes and platelets and a further improvement of the efficiency. Under the current circumstances, however, it has been difficult to determine ES cells excellent in terms of the efficiency of inducing megakaryocytes and platelets, until the megakaryocytes and platelets have finally been obtained.

Hence, taking into consideration the above-mentioned circumstances, the present inventors have decided that a first object of the present invention is to establish a method for obtaining megakaryocytes and platelets from iPS cells, and that another object of the present invention is to establish a method capable of stabilizing the efficiency of obtaining megakaryocytes and platelets.

Means for Solving the Problems

In the present studies, the present inventors have conducted intensive studies directed towards achieving the aforementioned objects. They have attempted to induce megakaryocytes and platelets from iPS cells, and as a result, they have established an induction method. In the attempt, the inventors have found that iPS cells derived from the same lot have heterogeneous characteristics, and they have also attempted to select cells capable of efficiently inducing megakaryocytes and platelets from this heterogeneous cell population at the early stage. As a result, they have found that cell clones exhibiting certain characteristics, for example, clones forming more sac-like structures, are excellent in terms of the efficiency of inducing megakaryocytes and platelets. By selecting such cells and inducing the differentiation thereof, it has become possible to stably and efficiently induce megakaryocytes or platelets.

Specifically, the present invention relates to a method for preparing megakaryocytes and platelets from iPS cells. More specifically, the present invention relates to the following (1) to (16):

(1) A first aspect of the present invention relates to "a sac-like structure enclosing hematopoietic progenitor cells, which is obtained by inoculating human-derived iPS cells onto feeder cells and then culturing the iPS cells under conditions suitable for inducing the differentiation of hematopoietic progenitor cells."

(2) A second aspect of the present invention relates to "the sac-like structure according to (1) above, wherein the conditions suitable for inducing the differentiation of hematopoietic progenitor cells involve the culture of the cells for 14 to 17 days in the presence of VEGF."

(3) A third aspect of the present invention relates to "the sac-like structure according to (1) or (2) above, which is characterized in that the feeder cells are C3H10T1/2 cells or OP9 cells."

(4) A fourth aspect of the present invention relates to "a method for producing blood cells, which comprises: selecting iPS cell clones having high ability to produce the sac-like structure according to any one of (1) to (3) above; separating cells forming the septum of the sac-like structure from hematopoietic progenitor cells, both of which are produced by the iPS cell clones; inoculating the obtained hematopoietic progenitor cells onto feeder cells; and culturing the hematopoietic progenitor cells under conditions suitable for inducing the differentiation of blood cells, so as to produce blood cells."

(5) A fifth aspect of the present invention relates to "the method according to (4) above, which is characterized in that the blood cells are megakaryocytes and platelets."

(6) A sixth aspect of the present invention relates to "the method according to (5) above, wherein the conditions suitable for inducing the differentiation of blood cells involve the culture of the cells for 7 to 9 days in the presence of TPO."

(7) A seventh aspect of the present invention relates to "the method according to (5) above, wherein the conditions suitable for inducing the differentiation of blood cells involve the culture of the cells for 7 to 9 days in the presence of TPO, SCF, and heparin."

(8) An eighth aspect of the present invention relates to "a megakaryocyte and/or a platelet produced by the method according to any of (5) to (7) above."

(9) A ninth aspect of the present invention relates to "a blood product comprising, as an active ingredient, a platelet produced by the method according to any of (5) to (7) above."

(10) A tenth aspect of the present invention relates to "a method for producing blood cells, which comprises: subjecting mouse-derived iPS cells to a liquid culture to form hematopoietic progenitor cells in the embryoids thereof; and further culturing the embryoids, so as to produce blood cells."

(11) An eleventh aspect of the present invention relates to "the method according to (10) above, which is characterized in that the blood cells are megakaryocytes and platelets."

(12) A twelfth aspect of the present invention relates to "the method according to (10) or (11) above, wherein the period of time at which the embryoids are further cultured is 5 to 7 days."

(13) A thirteenth aspect of the present invention relates to "the method according to any one of (10) to (12) above, wherein the conditions for further culturing the embryoids involve the culture of the embryoids in the presence of TPO and SCF for 3 to 5 days."

(14) A fourteenth aspect of the present invention relates to "a megakaryocyte and/or a platelet produced by the method according to any of (10) to (13) above."

(15) A fifteenth aspect of the present invention relates to "a blood product comprising, as an active ingredient, a platelet produced by the method according to any of (10) to (13) above."

(16) A sixteenth aspect of the present invention relates to "a kit for preparing platelets by the method according to any one of (4) to (7) and (10) to (13) above."

Effects of the Invention

Using the method of the present invention for inducing megakaryocytes and platelets from iPS cells (particularly, human iPS cells), it becomes possible to induce megakaryocytes and platelets more stably and efficiently than in the case of using ES cells.

According to the present invention, it becomes possible to prepare special blood cells for patients who require blood transfusion, which retain the genetic characteristics of the patients. As a result, it becomes possible to overcome problems regarding human leukocyte antigen (HLA) compatibility. In addition, it also becomes possible to avoid the generation of antiplatelet antibodies due to the mixing of the HLA-type blood of other people, which has been problematic in clinical sites.

Moreover, using the method of the present invention, desired blood cells can be efficiently obtained in vitro. In particular, with regard to humans, special platelets for particular individuals can be efficiently produced in relatively large quantities.

Furthermore, using the method of the present invention, the stable supply of a blood product comprising a platelet as an active ingredient can be realized.

In the human ES cell- and human iPS cell-derived platelets, the microtubular structures of granules and platelets containing various physiologically active substances for the platelets were retained as in the case of peripheral blood.

Figure 17:
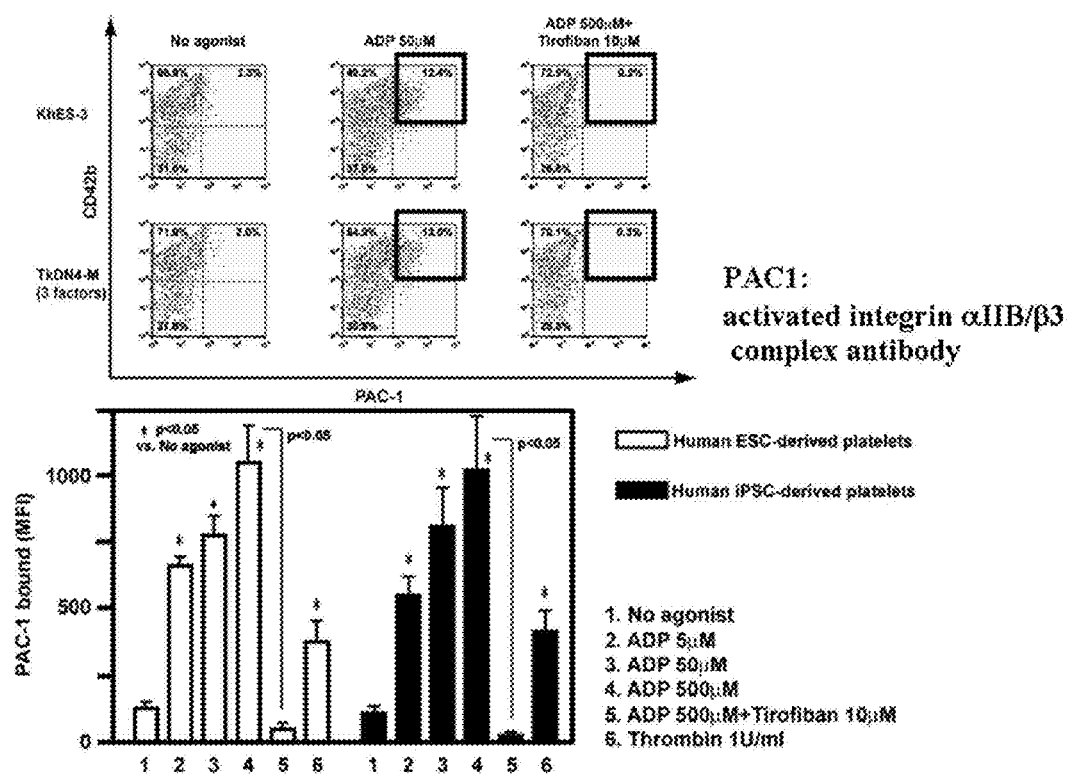

FIG. 17 shows the results obtained by analyzing the functions of human iPS cell-derived platelets (inside-out signal). The upper panels show representative FAC images. In human iPS cell-derived platelets (lower case), the activation of integrin (an increase in PAC1 antibody-positive platelets) was observed because of the presence of an important in vivo platelet activator ADP, as in the case of human ES cell-derived platelets (upper case). In the lower panel, human iPS cell-derived platelets (black bar graph) reacted with a low concentration (5 μM) of APD, and the reaction was increased dose-dependently, as in the case of human ES cell-derived platelets (white bar graph). The reaction with another activator thrombin could also be confirmed. The term "no agonist" indicates the results obtained without ADP.

BEST MODE FOR CARRYING OUT THE INVENTION

An embodiment of the present invention relates to a sac-like structure (sac) enclosing hematopoietic progenitor cells, which is obtained by inoculating iPS cells onto feeder cells and then culturing the iPS cells under conditions suitable for inducing the differentiation of hematopoietic progenitor cells. Since hematopoietic progenitor cells are condensed in this sac-like structure, the differentiation of various types of blood cells can be efficiently induced in vitro with the use of the sac-like structure. The term "sac-like structure" is used herein to mean a three-dimensional saccular structure (containing a space therein) derived from ES or iPS cells, which is formed with an endothelial cell population or the like and which contains blood progenitor cells therein. As for the details of such a sac-like structure, please refer to TAKAYAMA et al., BLOOD 2008, 111: 5298-5306, for example. Herein, the "iPS cells" is also referred to as artificial pluripotent stem cells or induced type pluripotent stem cells. The iPS cells are cells, which have acquired pluripotent differentiation ability equivalent to that of ES cells, as a result of the introduction of several types of transcription factor genes into somatic cells such as fibroblasts. Examples of known transcription factor genes necessary for acquiring pluripotent differentiation ability include Nanog, Oct3/4, Sox2, Klf4, c-Myc, and Lin28. By selecting several genes from these genes, for example, in the combination of Oct3/4, Sox2, Klf4 and c-Myc, or in the combination of Oct3/4, Sox2, Nanog and Lin28, or in the combination of Oct3/4, Sox2 and Klf4, and then introducing the thus selected genes into somatic cells such as fibroblasts, iPS cells can be established. With regard to the iPS cells used in the present invention, the method for establishing the cells is not limited. Other than the iPS cells established by the method involving the introduction of the above-described genes, either iPS cells established by a method of introducing genes other than the above-described genes, or iPS cells established by a method using a protein or a low-molecular-weight compound, may be used in the present invention.

Moreover, any types of "feeder cells" can be used, as long as they are cells contributing to induction of the differentiation of ES cells or iPS cells. For example, mouse embryonic fibroblasts, and preferably, a C3H10T1/2 cell line, OP9 cells, and the like can be used. When such "feeder cells" are used, it may be preferable to suppress the growth of the cells by exposure to radiation, etc.

As conditions for culturing iPS cells, conditions suitable for preparing a sac-like structure (hereinafter also referred to as "iPS-Sac") can be selected. These culture conditions are different depending on the organism species of iPS cells used. As an example, when human-derived iPS cells are used, IMDM, to which FBS in a final concentration of 15% has been added, can be used as a medium. Moreover, in the case of using a serum free medium, growth factors, supplements, and the like may be added to the medium, as appropriate. Furthermore, in order to efficiently form a sac-like structure from human-derived iPS cells, for example, VEGF may be added in a concentration of approximately 0 to 100 ng/ml, and more preferably, of approximately 20 ng/ml, to a medium. The culture environment is different depending on iPS cells used. For example, conditions consisting of 5% $CO_2$, and a temperature of 36° C. to 38° C., and preferably 37° C., can be applied. The culture period from the beginning of the culture until the formation of a sac-like structure is different depending on human iPS cells used. For example, the presence of the sac-like structure can be confirmed 14 to 17 days after the inoculation of the iPS cells on feeder cells.

The formed sac-like structure has a follicular structure. In the structure, a septum has been constituted with Flk1 (fetal liver kinase 1; one of mesodermal cell markers)-, CD31-, CD34-, or UEA-I lectin (*Ulex europaeus*. agglutinin-1)-positive cells. In this sac-like structure, hematopoietic progenitor cells are present in a concentrated state. In a case in which the differentiation of various types of blood cells is induced from the hematopoietic progenitor cells existing in the sac-like structure, it is necessary to separate the hematopoietic progenitor cells from cells constituting a septum. This separation is desirably carried out by physical means. For example, the septal cells can be separated from the hematopoietic progenitor cells by passing the cells through a sterilized sieve-like tool (e.g. cell strainer, etc.).

Another embodiment of the present invention relates to a method for producing various types of blood cells from hematopoietic progenitor cells separated from a sac-like structure. The obtained hematopoietic progenitor cells are inoculated onto feeder cells, and they are then cultured under conditions suitable for induction of the differentiation of desired blood cells. Examples of the "conditions suitable for induction of the differentiation of blood cells" include conditions involving the addition of any one of, or two or more of TPO, IL-1α, IL-3, IL-4, IL-5, IL-6, IL-9, IL-11, EPO, GM-CSF, SCF, G-CSF, Flt3 ligand, Heparin and the like, depending on the type of blood cells of interest. When the differentiation of megakaryocytes and platelets is induced, cells are cultured, for example, in the presence of TPO (10 to 200 ng/mL, and preferably approximately 100 ng/mL), or in the presence of TPO (10 to 200 ng/mL, and preferably approximately 100 ng/mL), SCF (10 to 200 ng/mL, and preferably approximately 50 ng/mL) and Heparin (10 to 100 U/mL, and preferably approximately 25 U/mL), for approximately 7 to 15 days. The culture environment is not particularly limited, as long as it is suitable for inducing the differentiation of blood cells in vitro. For example, the culture is carried out in 5% $CO_2$ and at a temperature of 36° C. to 38° C., and preferably at 37° C.

Figure 9:
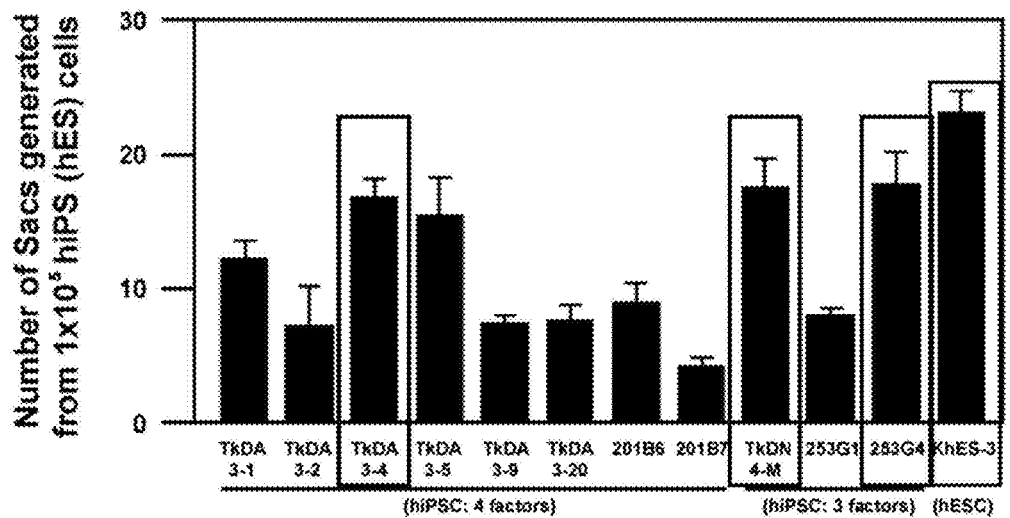
FIG. 9 shows the results obtained by comparing the efficiency of inducing iPS-Sacs among human iPS cell clones. The number of Sacs including blood cell progenitor cells on Day 15 of culture (the longitudinal axis of the graph) was counted. A difference in differentiation ability was observed among human iPS cell lines derived from the skin of the same lot (TkDA3-1, 2, 4, 5, 9 and 20). TkDA3-1, 2, 4, 5, 9 and 20 (established at the University of Tokyo) are human iPS cell lines produced from 4 factors (Oct3/4, Sox2, Klf4 and c-Myc) derived from the same skin cells; TkDN4-M (established at the University of Tokyo) is a human iPS cell line produced from 3 factors (the same factors as those described above, other than c-Myc) derived from skin cells; 201B6 and 201B7 (established at the Kyoto University) are human iPS cells lines produced from 4 factors derived from skin cells; and 253G1 and 253G4 (established at the Kyoto University) are human iPS cell lines produced from 3 factors derived from skin cells. In addition, KhES-3 is a human ES cell line having high blood cell differentiation ability, which was used as a control.

When megakaryocytes and platelets are produced from iPS cells, and particularly from human-derived iPS cells, since the efficiency of producing the above-described sac-like structures is different depending on iPS cell clones, iPS cell clones having a high efficiency of producing the sac-like structures have previously been selected, and various types of blood cells such as megakaryocytes and platelets are then produced from the sac-like structures produced by the selected iPS cell clones. As a result, many blood cells can be prepared more efficiently (please see FIG. 9). Herein, as an iPS cell clone having a "high" efficiency of producing sac-like structures, a clone forming 10 or more, and preferably 15 or more sac-like structures per $1\times10^5$ cells can be selected, for example.

A further embodiment of the present invention relates to a method, which comprises forming an embryoid (a cell population containing differentiation-induced, undifferentiated mesodermal cells) from mouse-derived iPS cells and then inducing the embryoid to differentiate into megakaryocytes and platelets. In the case of mouse ES cells, it is possible to form an embryoid without carrying out a co-culture with feeder cells such as OP9 cells and then to induce the formed embryoid to differentiate into undifferentiated mesodermal cells. In the case of mouse iPS cells as well, it is possible to induce the formed embryoid to differentiate into undifferentiated mesodermal cells under the same conditions as those in the case of mouse ES cells. As the culture conditions in this case, a medium used is different depending on iPS cells used. For example, IMDM containing FBS, human transferrin, etc., to which supplements and the like are further added, as appropriate, can be used. The culture environment is different depending on iPS cells used. For example, conditions consisting of 5% $CO_2$, and a temperature of 36° C. to 38° C., and preferably 37° C., can be applied. The culture period from the beginning of the culture until the formation of an embryoid is different depending on iPS cells used. For example, the presence of the embryoid can be confirmed 6 to 9 days after the beginning of the culture.

Subsequently, the embryoid is cultured under conditions suitable for induction of the differentiation of blood cells, so that it can be induced to differentiate into megakaryocytes and platelets. Examples of the "conditions suitable for induction of the differentiation of blood cells" include conditions involving the addition of any one of, or two or more of TPO, IL-1α, IL-3, IL-4, IL-5, IL-6, IL-9, IL-11, EPO, GM-CSF, SCF, G-CSF, Flt3 ligand, Heparin and the like. When the differentiation of megakaryocytes and platelets is induced, for example, TPO (10 to 200 ng/mL), SCF (1 to 200 ng/mL), IL-6 (approximately 1 to 100 ng/ml), IL-11 (approximately 1 to 100 ng/ml) and the like are added as appropriate, singly or in combination of two or more thereof, to a medium at an appropriate period. Approximately 3 to 5 days after the culture from the embryoid, megakaryocytes are induced, and approximately 7 to 9 days after the culture, platelets are induced. The culture environment is not particularly limited, as long as it is suitable for inducing the differentiation of blood cells in vitro. For example, the culture is carried out in 5% $CO_2$ and at a temperature of 36° C. to 38° C., and preferably at 37° C.

A further embodiment of the present invention relates to a kit for preparing platelets. This kit comprises a medium used for cell culture, serum, supplements such as growth factors (e.g. TPO, SCF, Heparin, IL-6, IL-11, etc.), antibiotics, and the like. In addition, the kit further comprises antibodies used to confirm markers existing in sac-like structures (e.g. antibodies reacting with Flk 1, CD31, CD34, UEA-I lectin, etc.) and the like. Reagents, antibodies and the like comprised in the kit are supplied into any type of vessel, in which constituents sustain their activity over a long period of time and they are not adsorbed thereon and are not degenerated thereby. For example, a sealed glass ampule contains a buffer included in the presence of a neutral nonreactive gas such as a nitrogen gas. Such an ampule is constituted with an organic polymer such as glass, polycarbonate or polystyrene, a ceramic, a metal, any other type of appropriate material commonly used to retain a reagent, or the like.

Since a platelet preparation is effectively used to prevent or improve a decrease in platelets due to leukemia, bone marrow transplantation or anticancer drug treatment, human platelets obtained by the present invention can be stably supplied in the form of a platelet preparation. A platelet preparation can be produced from the platelets produced by the method of the present invention, by recovering a fraction of a culture solution (for example, in the case of human-derived platelets, a culture solution fraction obtained on the approximately $22^{nd}$ to $28^{th}$ day of the culture of iPS cells), in which platelets released from megakaryocyte are abundant, and then removing megakaryocyte and other blood cells from the recovered culture solution, using a leukocyte-removing filter (which can be purchased, for example, from Terumo Corporation, Asahi Kasei Medical Co., Ltd., etc.) or the like, so as to remove components other than platelets. For the production of a blood preparation, taking into consideration the fact that platelets are instable in terms of preservation, other components used to stabilize platelets may be comprised. As conditions for stabilize platelets, a method well known to persons skilled in the art in the present technical field can be selected. More specifically, the obtained platelets (human ES cell-derived, washed platelets) can be converted to a platelet preparation by the following method, for example.

ACD-A solution and FFP (fresh frozen plasma; prepared from whole blood obtained as a result of blood donation, which contains all components other than blood components such as albumin and a clotting factor) are prepared at a ratio of 1:10, and radiation of 15-50 Gy is applied to the solution obtained as above. Thereafter, the resultant solution is preserved, while stirring at 20° C. to 24° C. The ACD-A solution is prepared by mixing 22 g of sodium citrate, 8 g of citric acid and 22 g of glucose with an injection solution to a total amount of 1 L.

When the above-described method is applied, the concentration of platelets is desirably set at approximately $1\times10^9$ platelets/mL, for example.

If GM6001 (a broad-range hydroxamic acid-based metalloprotease inhibitor) (Calbiochem, La Jolla, Calif., U.S.A.) is added, inactivation caused by the cleavage of a platelet functional molecule GPIb-V-IX or GPVI that occurs during cryopreservation or storage at room temperature can be prevented. The present inventors have confirmed that the inactivation of mouse ES cell-derived platelets can be prevented by this method. For more information on a mechanism underlying this platelet inactivation using human platelets, please see the references: Bergmeier, W et al., Cir Res 95: 677-683, 2004; and Gardiner, E E et al., J Thrombosis and Haemostasis, 5: 1530-1537, 2007.

As a vessel which contains a preparation containing platelets, a material that activates the platelets, such as a glass, is preferably excluded.

EXAMPLES

The present invention will be more specifically described in the following examples. However, these examples are not intended to limit the scope of the present invention.
1-1. Induction of Megakaryocytes and Platelets from Mouse iPS Cells
  1-1. Culture of Mouse Stromal Cell Line OP9
  OP9 cells were subcultured in α-Minimum Essential Medium (α-MEM; Invitrogen/GIBCO), to which 15% FBS, 2 mM L-glutamine, 100 U penicillin and 0.1 mg/mL streptomycin had been added. The medium was exchanged with a fresh one every other day. Cells, regarding which the number of subcultures was 30 or less after the primary culture, were used for experiments, in order not to change the characteristics of the cells.

1-2. Culture of Mouse Nanog-iPS Cells

Nanog-iPS cells (Nature, 448, 313-317 (2007)) (provided by Prof. Shinya Yamanaka, Kyoto University) were cultured in Iscove's Modified Dulbecco's Medium (IMDM; Invitrogen/GIBCO), to which 15% FBS, 300 µg/mL human transferrin (Sigma), 4.5 mM monothioglycerol (Sigma), 50 µg/mL ascorbic acid (Sigma), 0.1 mM 2-mercaptoethanol (Invitrogen/GIBCO), 2 mM L-glutamine, 100 U penicillin and 0.1 mg/mL streptomycin had been added, in a petri dish (Sterilin, U.S.A.). The culture was initiated using cells with a cell density of $2 \times 10^5$ cells per 10 mL of a culture solution in a petri dish, so as to attempt to form embryoids.

1-3. Induction of Megakaryocytes and Platelets

Figure 1:
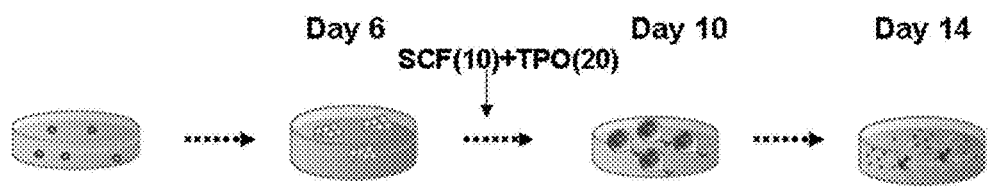
FIG. 1 is a view schematically showing a process of inducing platelets from mouse iPS cells.

Embryoids produced on Day 6 to 7 of culture were treated with 0.25% trypsin, and were then inoculated on confluent OP9 cells to a concentration of $1 \times 10^5$ cells/well. The cells were then cultured in αMEM, to which 20 ng/ml mouse TPO (Peprotec) and 10 ng/ml SCF had been added (FIG. 1).

Figure 2:
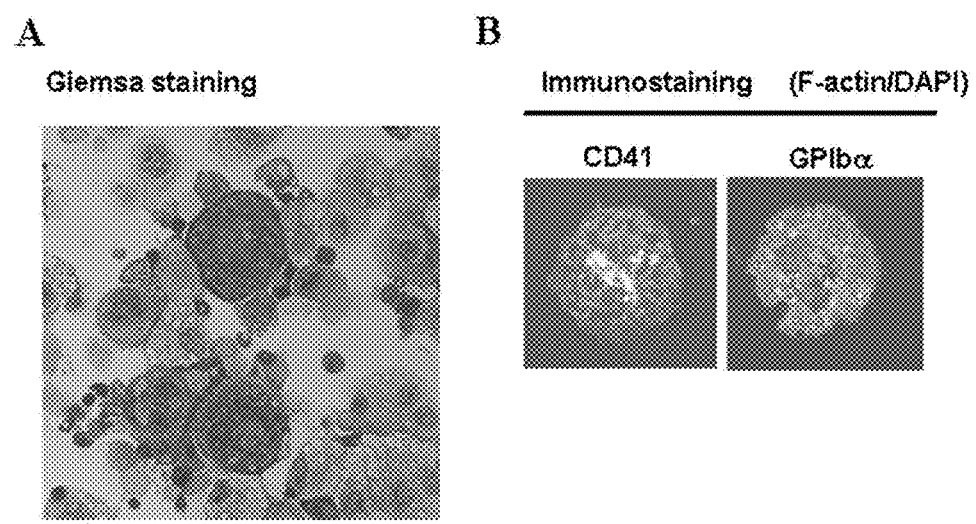
FIG. 2 shows the results obtained by cytospinning megakaryocytes that are proplatelets derived from mouse iPS cells on Day 10 of culture, and then performing Giemsa staining (FIG. 2(A)) and immunostaining (secondary staining method using Alexa 647) (FIG. 2(B)) with Alexa 488-phalloidin, DAPI, an anti-CD41 antibody and an anti-GPIbα antibody on the cells. The term "CD41" of FIG. 2(B) indicates a stained image of CD41-positive cells, and the term "GPIbα" of FIG. 2(B) indicates a stained image of GPIbα-positive cells.
Figure 3:
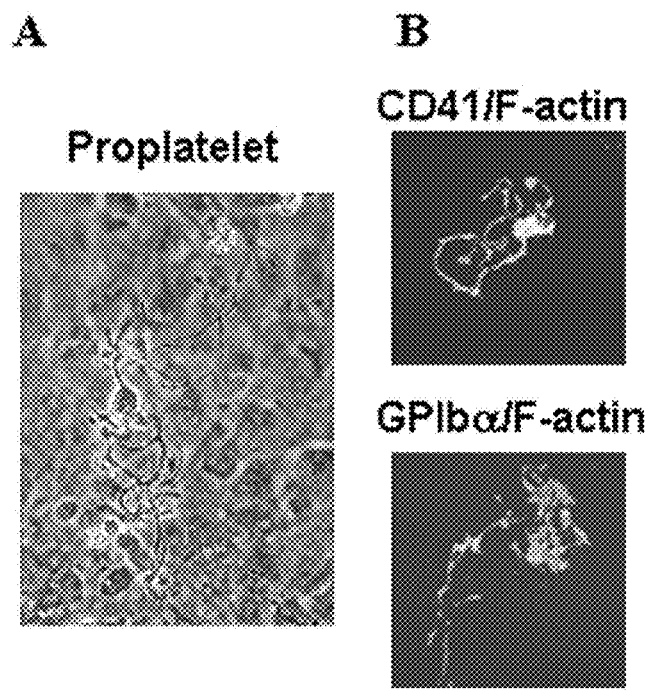
FIG. 3 shows the results obtained by performing a secondary staining with Alexa 647 on a phase-contrast microscope image (FIG. 3(A)) and immunostained images (FIG. 3(B)) with Alexa 488-phalloidin, an anti-CD41 antibody and an anti-GPIbα antibody of the proplatelets derived from mouse iPS cells on Day 14 of culture. The "CD41/F-actin" of FIG. 3(B) shows the results obtained by double staining with an anti-CD41 antibody (Alexa 647, red)/Alexa 488 (green)-phalloidin, and the "GPIbα/F-actin" shows the results obtained by double staining with an anti-GPIbα antibody (Alexa 647, red)/Alexa 488 (green)-phalloidin.
Figure 4:
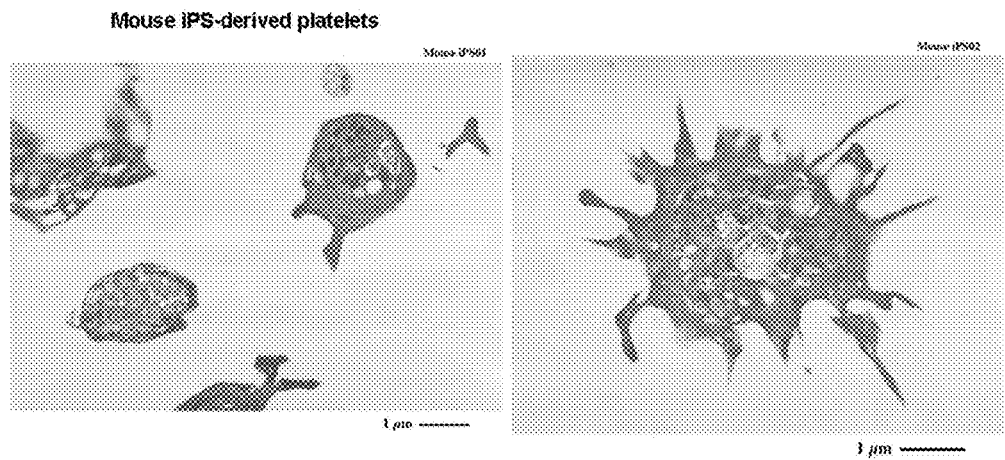
FIG. 4 shows electron microscope images of platelets induced from mouse iPS cells on Day 14 of culture.
Figure 5:
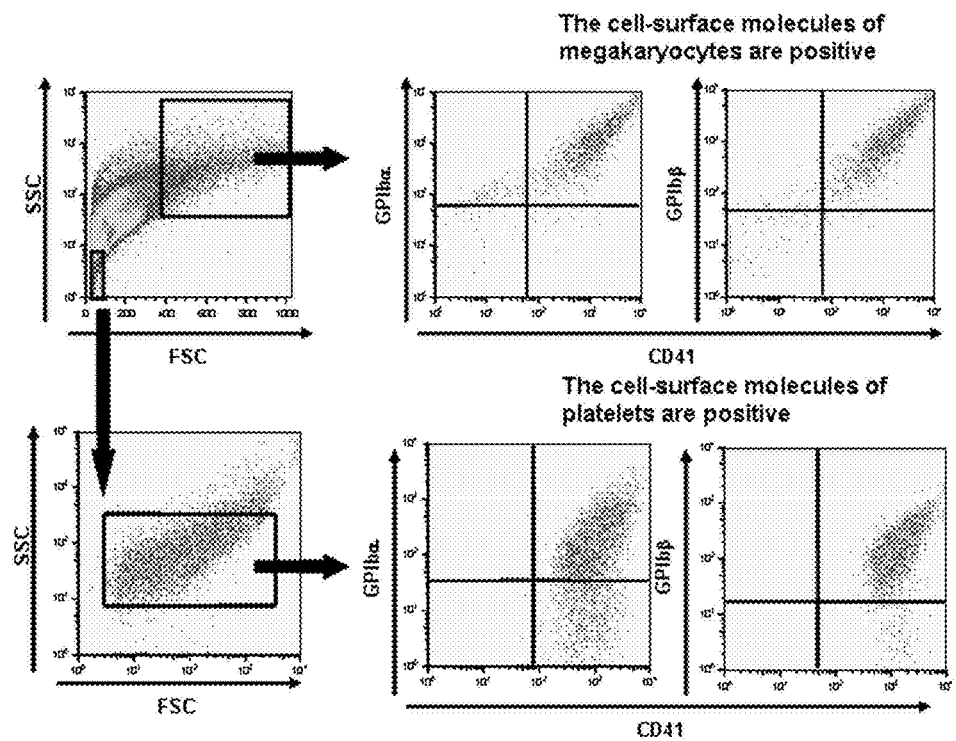
FIG. 5 shows the results obtained by analyzing with a flow cytometer cells derived from mouse iPS cells on Day 10 of culture (upper view) and on Day 14 of culture (lower view).

Ten days after the initiation of the culture, $CD41^+$ $GPIb\alpha^+$ mature megakaryocytes were induced (FIG. 2 and the upper view of FIG. 5). Thereafter, fourteen days after the continuous culture, $CD41^+$ $GPIb\alpha^+$ platelets were induced (FIG. 3 and the lower view of FIG. 5). The thus induced platelets had the same morphological characteristics as those of peripheral blood-derived platelets (FIG. 4).

Figure 6:
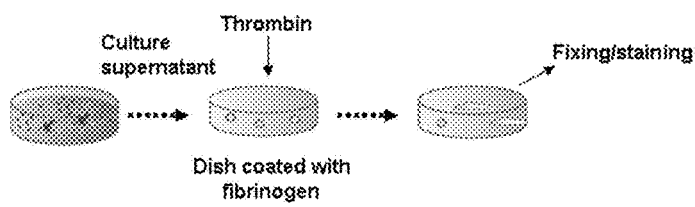
FIG. 6 is a view showing the observation of the shape change of mouse iPS cell-derived platelets with respect to thrombin. A supernatant was recovered on Day 14 of culture, it was then added to a dish coated with fibrinogen, and a platelet activity stimulator (thrombin) was then added thereto so as to stimulate it (upper view). By the addition of thrombin, platelets produced from the iPS cells are clearly extended, so that they have a shape capable of contributing to form stable blood clots (lower view). As a result, an image stained with an αIIβ antibody (secondary staining with Alexa 647) and with Alexa 488-phalloidin is shown (lower view).
Figure 6:
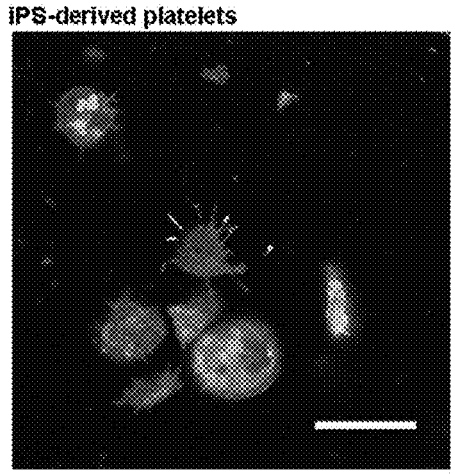

Thereafter, the functions of the thus obtained platelets were analyzed. A culture supernatant, into which the platelets had been released, was added to a fibrinogen-coated dish, and it was then stimulated with thrombin (the upper view of FIG. 6). As a result, cell spreading characteristic for platelets was observed. From this result, it became clear that platelets having the same characteristics as those of in vivo platelets can be induced from mouse iPS cells.

2. Induction of Megakaryocytes and Platelets from Human iPS Cells 2-1. Preparation of Sac-Like Structures (iPS-Sacs)

Cell lines used in the present example, 201B6 (in which Oct3/4, Klf4, Sox2 and c-Myc had been introduced into skin cells; Cell, 131, 861-872 (2007)) and 253G1 (in which Oct3/4, Klf4 and Sox2 had been introduced into skin cells; Nature Biotech., 26, 101-106 (2008)), were provided by Prof. Shinya Yamanaka, Kyoto University. Moreover, TkDA3-1, TkDA3-2, TkDA3-4, TkDA3-5, TkDA3-9 and TkDA3-20 (which had been newly established at the University of Tokyo, and which had been prepared by introducing Oct3/4, Klf4, Sox2 and c-Myc into skin cells) and TkDN4-M (in which Oct3/4, Klf4 and Sox2 had been introduced into skin cells; established at the University of Tokyo) were used. Further, as feeder cells, there were used mouse embryo-derived cells, a C3H10T1/2 cell line, provided by BioResource center, Riken Tsukuba Institute, or an OP9 cell line provided by Prof. Tooru Nakano at Graduate School of Medicine, Faculty of Medicine, Osaka University. On the day before the differentiation experiment, the C3H10T1/2 cells were inoculated on a dish coated with 0.1% gelatin at a cell density of $6 \times 10^5$ cells/a 10 cm dish. On the day of the differentiation experiment, the C3H10T1/2 cells were exposed to 50-Gy radiation, in order to suppress the growth of the cells. The resultant cells were used as feeder cells. Alternatively, when the OP9 cell line was used as feeder cells, the cells were exposed to 50-Gy radiation on the day before the differentiation experiment, and were then replated on another dish before use.

Human iPS cells were inoculated on the OP9 cells or the C3H10T1/2 cells in IMDM (IMDM; Invitrogen/GIBCO), to which 15% FBS (JRH BIOSCIENCES, U.S.A.), 2 mM L-glutamine (Invitrogen), an ITS supplement (10 µg/ml insulin, 5.5 mg/ml transferrin and 5 ng/ml sodium selenite) (Sigma), 50 µg/ml ascorbic acid (Sigma), 0.45 mM MTG (Sigma) and 20 ng/ml VEGF (R & D Systems) had been added, and the cells were then cultured.

Figure 7:
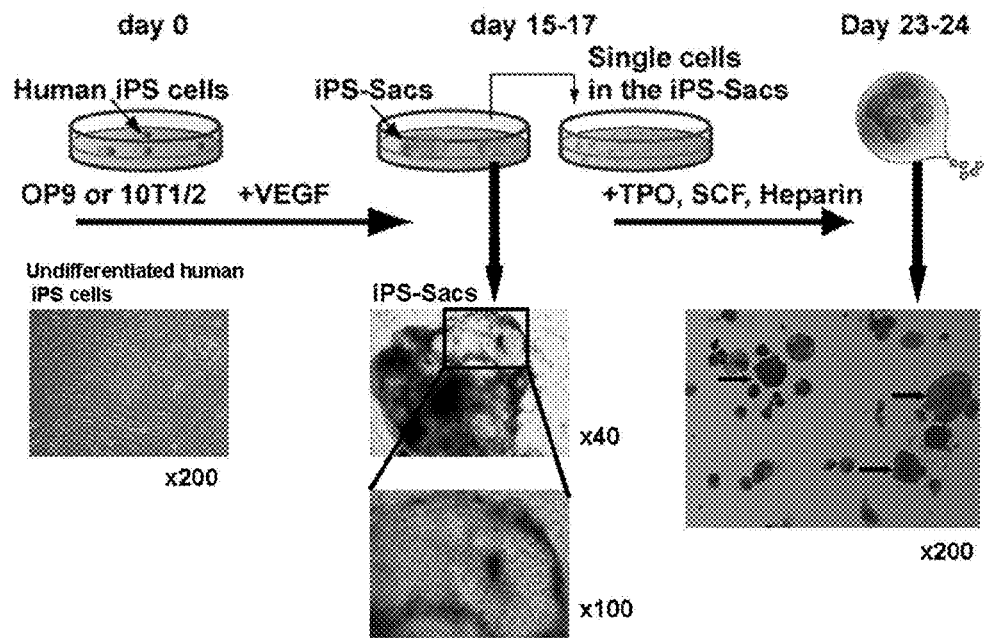
FIG. 7 shows a process of forming Sac structures from human iPS cells (201B6 line) and then inducing megakaryocytes and platelets therefrom. The upper view schematically shows the process of culture, and each photograph in the lower view shows iPS-Sacs and megakaryocytes that are induced in the culture process. The lower photographs show, from the left side, undifferentiated iPS cells on Day 0 of culture (an image observed under a phase-contrast microscope), iPS-Sacs induced from the iPS cells (an image observed on Day 17 of culture), and megakaryocytes (an image observed after Giemsa staining on Day 23 to 24 of culture), respectively.
Figure 10:
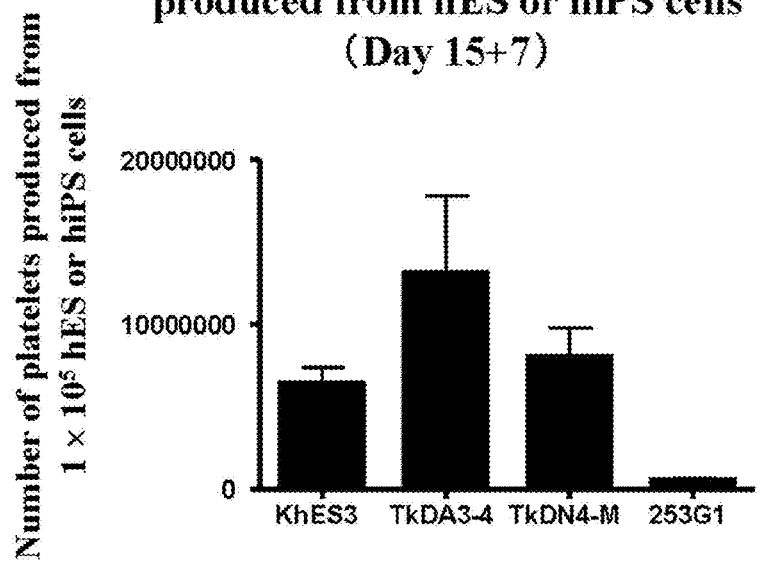
FIG. 10 shows the results obtained by analyzing the platelet-inducing ability of clones having different Sac-forming ability, selected from among the iPS cells shown in FIG. 9.

Fifteen to seventeen days after completion of the culture, a large number of sac-like structures containing blood cell-like cells therein were observed (FIG. 7, iPS-Sacs).

iPS cell clones are derived from a heterogeneous cell line (heterogeneity), although they have been established using, for example, 4 factors. Thus, even if such iPS cell clones were produced from the same type of skin cells, their differentiation ability varied. Accordingly, in the case of human iPS cells, clones suitable for differentiation can be selected by previously performing a screening (for example, the selection of clones that form a larger amount of sac-like structures). Thus, clones used for more efficient induction of the differentiation of blood cells can be easily selected (see FIG. 9). Actually, clones having different Sac-forming ability were selected from the iPS cells shown in FIG. 9, and the selected clones were then compared with one another in terms of platelet-inducing ability. Specifically, iPS cells (TkDA3-4, TkDN4-M and 253G1) and ES cells (KhES3) were used ($1 \times 10^5$ cells). The number of the finally obtained platelets was counted (FIG. 10). FIG. 10 suggested that iPS cells (TkDA3-4 and TkDN4-M) having high Sac-forming ability would easily form Sacs containing a large number of blood progenitor cells, and that the final number of platelets would be increased.

2-2. Colony Assay

Figure 11:
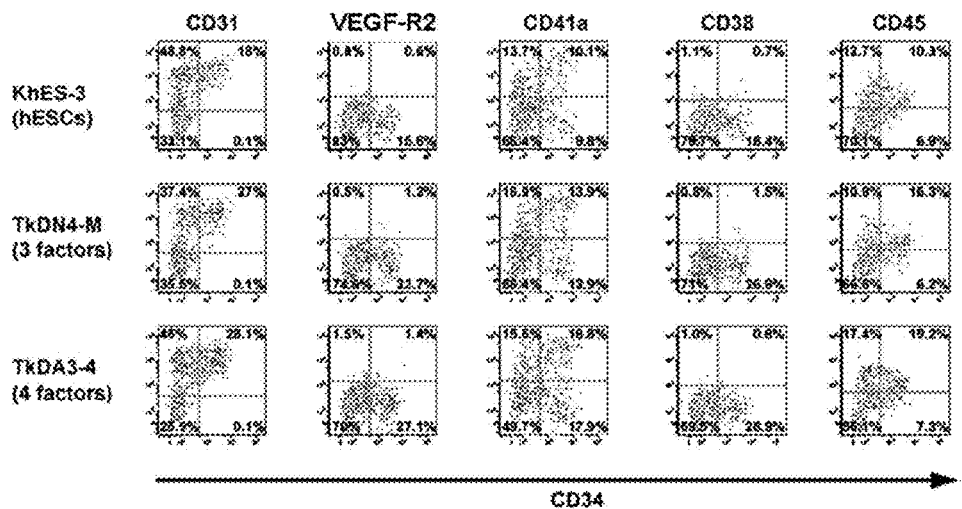
FIG. 11 shows the results obtained by analyzing the surface antigens of hematopoietic progenitor cells, which are derived from human ES cells and human iPS cells. Comparisons were made among human ES cell (upper case)-derived hematopoietic progenitor cells, TkDN4-M having high differentiation ability (3 factors; middle case), and TkDA3-4 (4 factors; lower case)-derived hematopoietic progenitor cells. CD31-positive/CD34-positive cells used as common markers for undifferentiated blood/vessel endothelium and CD34-positive/CD41a-positive cells used as markers for megakaryocyte progenitor cells were expressed at the same frequency as in the case of ES cells.
Figure 12:
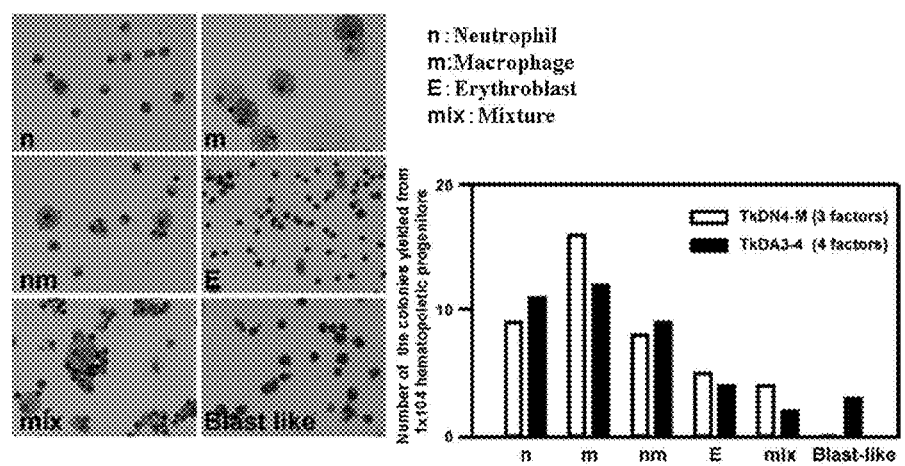
FIG. 12 shows the analysis of human iPS cell-derived blood cell colonies. Blood progenitor cells derived from TkDN4-M (3 factors) and blood progenitor cells derived from TkDA3-4 (4 factors) were each inoculated on a methylcellulose semisolid medium, and the two types of cells were then compared in terms of blood cell differentiation ability. The left view shows Giemsa-stained images of representative blood cell systems. The right view shows the frequency of colony-forming cells (wherein the longitudinal axis indicates the number of colonies derived from $1 \times 10^4$ blood cell progenitor cells). Only TkDA3-4 formed blast-like colonies (the lower right panel in the left view), but others had the same level of ability to differentiate into blood cells.

The cell-surface molecules of hematopoietic progenitor cells in sac-like structures were examined. As a result, it was found that CD31-positive/CD34-positive cells known as common markers for undifferentiated blood/blood vessel endothelium were expressed at the same frequency as that of ES cells, and that CD34-positive/CD41a cells known as markers for megakaryocyte progenitor cells were also expressed as in the case of ES cells (FIG. 11). In addition, their colony-forming ability was the same as that of human ES cells (FIG. 12). Blast-like colonies were observed in the human iPS cell line (4 factors) TkDA3-4 (blast-like, FIG. 12), and thus, a risk of canceration (leukemogenesis) was suggested.

2-3. Induction of Megakaryocytes/Platelets

Figure 8:
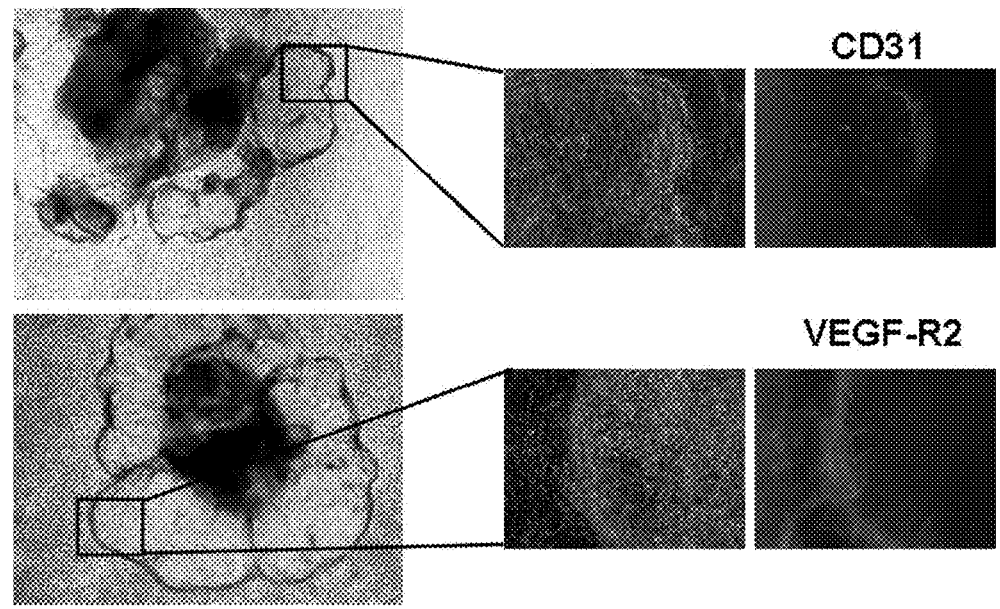
FIG. 8 shows immunostained images of iPS-Sacs. Such an iPS-Sac was constituted with CD31-positive and VEGF-R2-positive endothelial cells, as an with ES-Sac.
Figure 15:
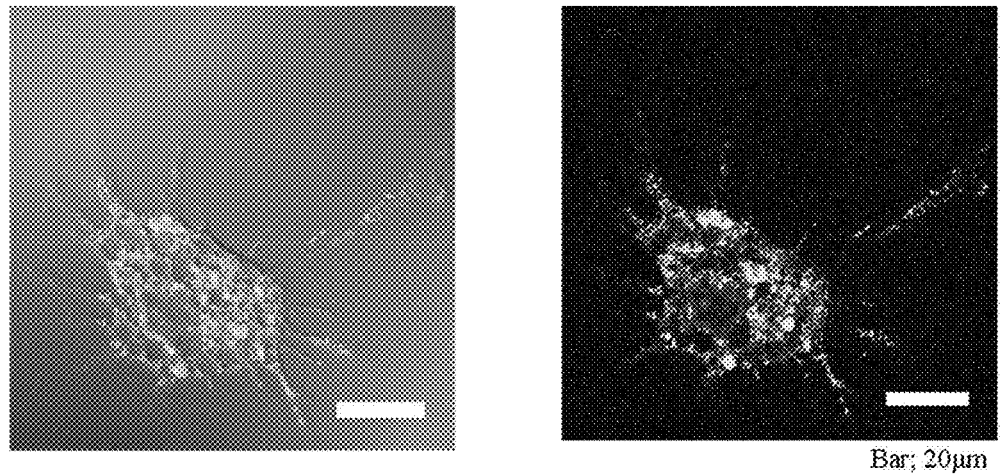
FIG. 15 is a view showing the observation of the shapes of platelets released from megakaryocytes. Floating cells on Day 17 to 18 after the culture were stained with Alexa 488-bound CD41a antibodies and were then observed under a fluorescence microscope (right view). The left view shows the image observed in a bright field according to a differential interference method.

Subsequently, sac-like structures were picked up under a phase-contrast microscope, using a P-1000 pipette. Thereafter, blood cells were separated from the sac-like structures, using a 70 µm cell strainer. The blood cells were inoculated at a cell density of 2 to $3 \times 10^4$/well on radiated C3H10T1/2 cells that had been newly prepared on a 6-well plate ($6 \times 10^5$ cells/a 6-well plate). The cells were then cultured in IMDM (IMDM; Invitrogen/GIBCO), to which 15% FBS (JRH BIOSCIENCES, U.S.A.), 2 M L-glutamine (Invitrogen), an ITS supplement (10 µg/ml insulin, 5.5 mg/ml transferrin and 5 ng/ml sodium selenite) (Sigma), 50 µg/ml ascorbic acid (Sigma), 0.45 mM MTG (Sigma), 100 ng/ml human TPO (Peprotec), 50 ng/ml SCF and 25 U/ml Heparin had been added, so as to induce megakaryocytes/platelets (FIGS. 7, 8 and 15).

Figure 13:
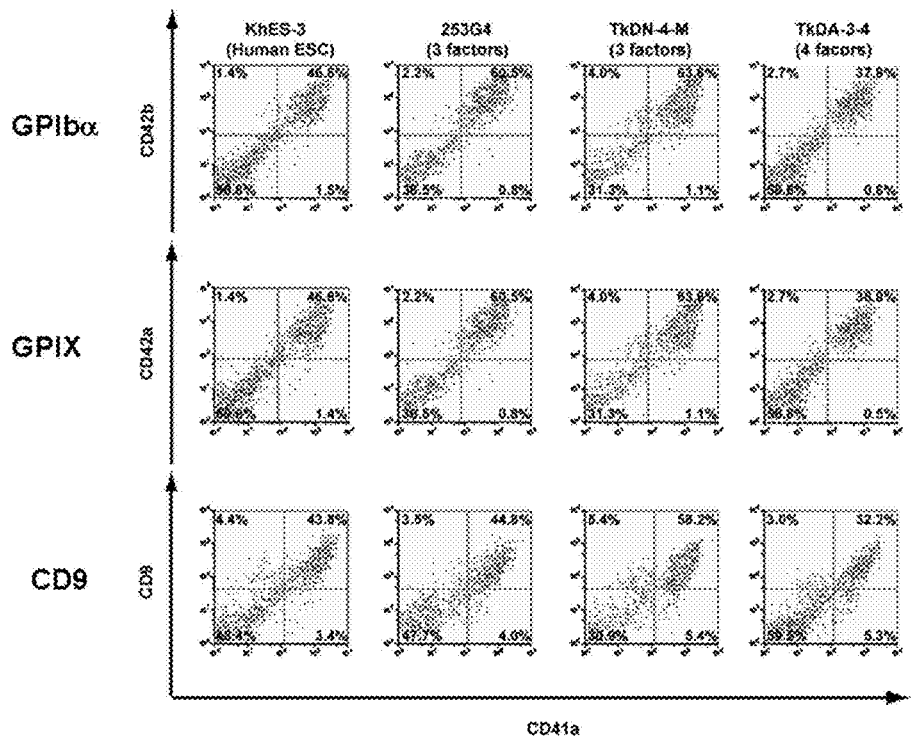
FIG. 13 shows the results obtained by analyzing floating cell components in the culture solution on Day 17 to 18 after the culture with a flow cytometer. The x-axis indicates CD41a, and the y-axis indicates CD42b, CD42a and CD9. From the left side, individual graph columns indicate KhES-3 (human ES cells), 253G4 (3-factor human iPS cells), TkDN4-M (3-factor human iPS cells) and TkDA3-4 (4-factor human iPS cells), respectively. CD42a and CD42b used as markers for mature megakaryocytes were expressed at the same level as in human ES cell-derived megakaryocytes.
Figure 14:
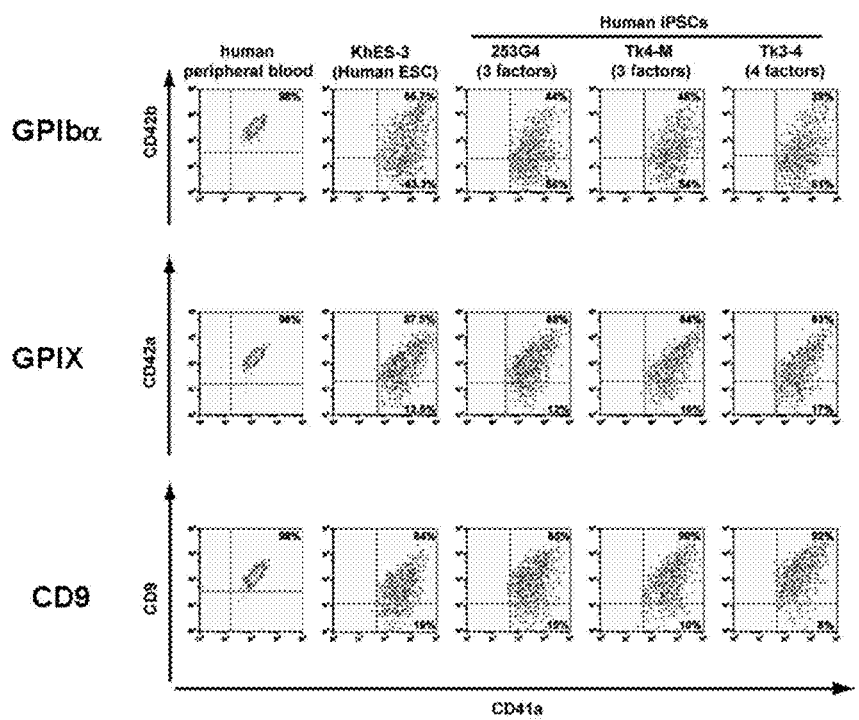
FIG. 14 shows the results obtained by analyzing the surface antigens of platelets derived from human iPS cells. Platelets, which were released into a culture supernatant on Day 24 of culture, were analyzed using a flow cytometer. The x-axis indicates CD41a, and the y-axis indicates CD42b, CD42a and CD9. From the left side, individual graph columns indicate human peripheral blood platelets, KhES-3 (human ES cells)-derived platelets, 253G4 (3-factor human iPS cells)-derived platelets, TkDN4-M (3-factor human iPS cells)-derived platelets, and TkDA3-4 (4-factor human iPS cells)-derived platelets, respectively. CD41a, CD42a and CD9, which are functional molecules important for platelets, were expressed at the same level as in the case of peripheral blood-derived platelets. On the other hand, the expression of CD42b was somewhat decreased in some of human ES cell- and human iPS cell-derived platelets (upper panel).
Figure 16:
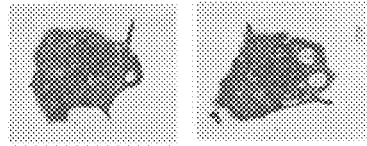
FIG. 16 shows the electron microscope images of human peripheral blood-, human ES cell- and human iPS cell-derived platelets, and human iPS cell-derived megakaryocytes.
Figure 16:
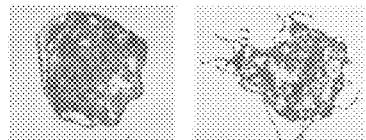
Figure 16:
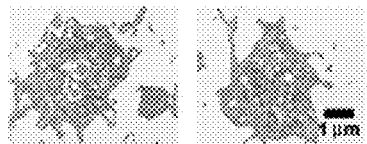
Figure 16:
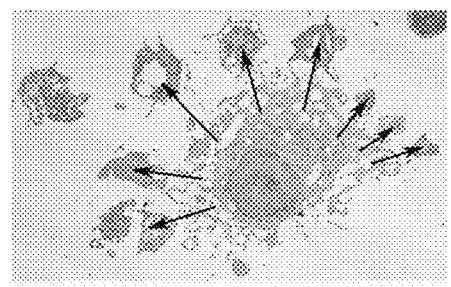

Floating cell components obtained 23 to 24 days after the culture of 253G1 (the cell line established at the Kyoto University), 201B6 (the cell line established at the Kyoto University), TkDA3-4 (the cell line established at the University of Tokyo) and TkDN4-M (the cell line established at the University of Tokyo) cell lines were analyzed using a flow cytometer, so that the characteristics of cell-surface antigens were examined. As a result, megakaryocyte- and platelet-specific surface molecule antigens, namely, human CD41a (integrin αIIb), and human CD42b (GPIbα), CD42a (GPIX) and CP9 positive cells were observed (FIG. 13: megakaryocytes; FIG. 14: platelets). Moreover, morphological characteristics shown during the release of platelets from megakaryocytes were also confirmed (FIGS. 15 and 16).

Subsequently, the activation of integrin by a platelet activator was analyzed. As a result, as with in human ES cell-derived platelets (the upper case in the lower panel, FIG. 17), the activation of integrin by a platelet activator ADP important in vivo (an increase in PAC1 antibody-positive platelets) was observed in human iPS cell-derived platelets (the lower case in the upper panel, FIG. 17). Moreover, as with human ES cell-derived platelets (the white bar graph, the lower panel, FIG. 17), human iPS cell-derived platelets (the black bar graph, the lower panel, FIG. 17) were reacted with even a low concentration (5 μM) of ADP, and the reaction was increased in a dose-dependent manner. Furthermore, the reaction of the cells with another activator thrombin could also be confirmed (No. 6 in the lower panel, FIG. 17). From these results, it became apparent that platelets produced from iPS cells exhibit the same functionality as that of human ES cell-derived platelets.

From the above results, it became clear that megakaryocytes and platelets can be efficiently induced from human iPS cells by the method of the present invention.

Industrial Applicability

According to the present invention, it becomes possible to provide platelets capable of overcoming problems regarding HLA compatibility. Accordingly, it becomes possible to supply special platelets for patients who require blood transfusion. As a result, it also becomes possible to overcome problems regarding platelet destruction due to the generation of antiplatelet antibodies.

The invention claimed is:

1. A method for producing blood cells, the method comprising:
    establishing clonal populations of human-derived induced pluripotent stem (iPS) cells;
    plating the iPS cells onto OP9 cells or 10T1/2 cells, and then culturing the iPS cells under conditions suitable for inducing differentiation of hematopoietic progenitor cells, thereby forming sac-like structures containing said hematopoietic progenitor cells;
    selecting human-derived iPS cell clones forming 10 or more sac-like structures per $1 \times 10^5$ cells;
    plating the selected iPS cell clones onto OP9 cells or 10T1/2 cells, and then culturing under conditions suitable for inducing differentiation of hematopoietic progenitor cells, thereby forming sac-like structures containing said hematopoietic progenitor cells; wherein each of the sac-like structures takes a follicular structure and has septa composed of UEA-1 lectin positive cells;
    separating cells forming the septum of the sac-like structures from the hematopoietic progenitor cells, both of which are produced by the iPS cell clones;

2. The method of claim 1, wherein the conditions suitable for inducing the differentiation of blood cells involve the culturing of the cells for 7 to 9 days in the presence of TPO, SCF, and heparin.

3. The method of claim 1, wherein the iPS cells are derived from introducing Oct 3/4, Sox 2, Klf4 and c-Myc into somatic cells.

* * * * *